(12) United States Patent
Barry et al.

US009421302B2

(10) Patent No.: US 9,421,302 B2
(45) Date of Patent: *Aug. 23, 2016

(54) INJECTABLE FIBRIN COMPOSITION FOR BONE AUGMENTATION (75) Inventors: John J. Barry, Vienna (AT); Andreas Goessl, Vienna (AT); Heinz Gulle, Gross Enzerdorf (AT); Monika Mangold, Vienna (AT); Melitta Bilban, Vienna (AT)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 174 days.

This patent is subject to a terminal disclaimer.

(21) Appl. No.: 11/736,518

(22) Filed: Apr. 17, 2007

(65) Prior Publication Data

US 2007/0275028 A1 Nov. 29, 2007

Related U.S. Application Data (60) Provisional application No. 60/808,709, filed on May 26, 2006.

(51) Int. Cl.
| | | |
|---|---|---|
| *A01N 43/00* | (2006.01) | |
| *A61K 31/33* | (2006.01) | |
| *A61F 13/00* | (2006.01) | |
| *A61K 38/48* | (2006.01) | |
| *A61L 27/26* | (2006.01) | |
| *A61L 24/00* | (2006.01) | |
| *A61L 24/02* | (2006.01) | |
| *A61L 24/10* | (2006.01) | |
| *A61L 27/12* | (2006.01) | |
| *A61L 27/22* | (2006.01) | |
| *A61L 27/54* | (2006.01) | |
| *A61L 27/58* | (2006.01) | |
| *A61F 2/28* | (2006.01) | |
| *A61F 2/44* | (2006.01) | |
| *A61F 2/46* | (2006.01) | |
| *A61F 2/30* | (2006.01) | |

(52) U.S. Cl.
CPC ............ *A61L 27/26* (2013.01); *A61L 24/0015* (2013.01); *A61L 24/0042* (2013.01); *A61L 24/02* (2013.01); *A61L 24/106* (2013.01); *A61L 24/108* (2013.01); *A61L 27/12* (2013.01); *A61L 27/225* (2013.01); *A61L 27/227* (2013.01); *A61L 27/54* (2013.01); *A61L 27/58* (2013.01); *A61F 2/28* (2013.01); *A61F 2/44* (2013.01); *A61F 2/4601* (2013.01); *A61F 2002/2817* (2013.01); *A61F 2002/2828* (2013.01); *A61F 2002/30062* (2013.01); *A61F 2002/30677* (2013.01); *A61F 2210/0004* (2013.01); *A61F 2310/00293* (2013.01); *A61F 2310/00377* (2013.01); *A61L 2300/202* (2013.01); *A61L 2300/418* (2013.01); *A61L 2300/44* (2013.01); *A61L 2300/622* (2013.01); *A61L 2400/06* (2013.01); *A61L 2430/02* (2013.01)

(58) Field of Classification Search
None
See application file for complete search history.

(56) References Cited

U.S. PATENT DOCUMENTS

| | | | |
|---|---|---|---|
| 4,696,812 A | 9/1987 | Silbering et al. | |
| 4,737,411 A | 4/1988 | Graves et al. | |
| 4,969,888 A | 11/1990 | Scholten et al. | |
| 5,108,404 A | 4/1992 | Scholten et al. | |
| 5,242,683 A * | 9/1993 | Klaveness | 424/9.35 |
| 5,549,904 A | 8/1996 | Juergensen et al. | |
| 5,618,549 A | 4/1997 | Patat et al. | |
| 5,736,132 A | 4/1998 | Juergensen et al. | |
| 5,752,974 A | 5/1998 | Rhee et al. | |
| 5,856,356 A | 1/1999 | Tsouderos et al. | |
| 5,861,043 A | 1/1999 | Carn | |
| 6,096,309 A | 8/2000 | Prior et al. | |
| 6,214,368 B1 * | 4/2001 | Lee et al. | 424/423 |
| 6,258,778 B1 | 7/2001 | Rodgers et al. | |
| 6,287,341 B1 | 9/2001 | Lee et al. | |
| 6,605,294 B2 | 8/2003 | Sawhney | |
| 6,607,535 B1 | 8/2003 | Chan | |
| 6,703,038 B1 | 3/2004 | Schaefer et al. | |
| 6,905,723 B2 | 6/2005 | Li | |
| RE39,192 E | 7/2006 | MacPhee et al. | |
| 2001/0016646 A1 * | 8/2001 | Rueger et al. | 530/840 |
| 2002/0091411 A1 | 7/2002 | Saker et al. | |
| 2003/0194389 A1 | 10/2003 | Porter | |
| 2004/0048947 A1 | 3/2004 | Lidgren et al. | |
| 2004/0068266 A1 * | 4/2004 | Delmotte | 606/92 |

(Continued)

FOREIGN PATENT DOCUMENTS

| | | |
|---|---|---|
| EP | 0 166 263 A | 1/1986 |
| EP | 166263 | 1/1986 |

(Continued)

OTHER PUBLICATIONS

What is Viscosity?in http://www.myprocessengineers.com/2012/02/what-is-viscosity.html.*

(Continued)

*Primary Examiner* — Jared D Barsky
(74) *Attorney, Agent, or Firm* — Kilpatrick Townsend & Stockton LLP (57) ABSTRACT

The present invention relates to a biodegradable injectable composition for bone augmentation comprising fibrin, a contrast agent and calcium salt-containing particles, as well as a method for bone augmentation in a patient suffering from a bone disorder comprising injecting said composition into a non-mineralized or hollow portion of said bone.

26 Claims, 2 Drawing Sheets

(56) References Cited

U.S. PATENT DOCUMENTS

| | | |
|---|---|---|
| 2004/0101960 A1 | 5/2004 | Schaefer et al. |
| 2004/0241314 A1 | 12/2004 | Li |
| 2005/0119746 A1 | 6/2005 | Lidgren |
| 2005/0136038 A1 | 6/2005 | de Bruijn et al. |
| 2005/0142211 A1 | 6/2005 | Wenz |
| 2006/0089715 A1 | 4/2006 | Truckai |
| 2006/0216321 A1 | 9/2006 | Lyu et al. |
| 2007/0073307 A1 | 3/2007 | Scribner et al. |
| 2007/0276505 A1 | 11/2007 | Barry et al. |
| 2008/0058828 A1 | 3/2008 | Reiley et al. |
| 2008/0065091 A1 | 3/2008 | Scribner et al. |
| 2008/0066495 A1 | 3/2008 | Moimas et al. |
| 2008/0241072 A1 | 10/2008 | Barry et al. |

FOREIGN PATENT DOCUMENTS

| | | | |
|---|---|---|---|
| EP | 1405647 | | 4/2004 |
| EP | 1655042 | | 5/2006 |
| EP | 1741436 | A1 | 1/2007 |
| JP | 60-256460 | | 12/1985 |
| JP | 07-213598 | A | 8/1995 |
| WO | 91/12032 | | 8/1991 |
| WO | 91/17777 | | 11/1991 |
| WO | 94/28949 | | 12/1994 |
| WO | WO 95/21634 | | 8/1995 |
| WO | 96/21628 | | 7/1996 |
| WO | WO 97/15188 | | 5/1997 |
| WO | WO 9823297 | A2 * | 6/1998 |
| WO | WO 00/07639 | | 2/2000 |
| WO | 03-053488 | | 7/2003 |
| WO | WO 03/053488 | A1 | 7/2003 |
| WO | 2004-078223 | A1 | 9/2004 |
| WO | 2004/098619 | A2 | 11/2004 |
| WO | 2005/082385 | | 9/2005 |
| WO | WO 2005/086697 | | 9/2005 |
| WO | 2006-005269 | | 1/2006 |
| WO | WO2006/007623 | * | 1/2006 ............ A61K 38/18 |
| WO | 2006-050268 | | 5/2006 |
| WO | 2006/050269 | | 5/2006 |
| WO | WO 2006/072622 | A2 | 7/2006 |
| WO | WO 2006/072623 | A1 | 7/2006 |
| WO | WO 2006/073711 | A2 | 7/2006 |
| WO | WO 2006072622 | A2 * | 7/2006 ............ A61K 38/29 |
| WO | WO 2006072623 | A1 * | 7/2006 ......... A61K 38/1875 |
| WO | WO 2006073711 | A2 * | 7/2006 ......... A61K 38/1875 |

OTHER PUBLICATIONS

Taylor et al., "Surgical Release of the Snapping Iliopsoas Tendon," The Journal of Bone and Joint Surgery, vol. 77-B, No. 6, Nov. 1995.*
GE Healthcare, Omnipaque (iohexol) Injection.*
Trout, A.T., "New Fractures After Vertebroplasty: Adjacent Fractures Occur Significantly Soonr", 2006, J Neuroradiol, vol. 27, pp. 217-223.
Isogai, et al., "Formation of Phalanges and Small Joints by Tissue-Engineering," The Journal of Bone and Joint Surger, Mar. 3, 1999, pp. 306-316, vol. 81-A, No. 3.
Achtari et al., Gynakol Geburtschilfliche Rundsch, 46:39-44 (2006) (Abstract).
Barth et al., JAVMA, 226(1):73-76 (2005).
Brown et al., Am. J. Pathol., 142(1):273-283 (1993).
Zhi et al., J. Long-Term Effects of Medical Implants, 15(4):375-388 (2005).
International Search Report and Written Opinion for PCT/US2008/058146 mailed Oct. 15, 2009.
International Preliminary Report on Patentability for for PCT/US2008/058146 mailed Oct. 29, 2009.
Parikit, SN, "Bone Graft Substitutes: Past, Present, Future," 2002, J. Postgrad Med, vol. 48, pp. 142-148.
Ammann, P., "Strontium ranelate: A physiological approach for an improved bone quality," Bone vol. 38 (2006): pp. S15-S18.
Canalis, et al., "The Divalent Strontium Salt S12911 Enhances Bone Cell Replication and Bone Formation In Vitro," Bone vol. 18, No. 6 (1996): pp. 517-523.
Close, P., et al., "Developments in the pharmacotherapeutic management of osteoporosis," Expert Opinion Pharmacotherapy vol. 7, No. 12 (2006): pp. 1603-1615.
Dahl, S.G., et al., "Incorporation and Distribution of Strontium in Bone," Bone vol. 28, No. 4 (2001): pp. 446-453.
Ferraro, E.F., et al., "A Comparison of the Effects of Strontium Chloride and Calcium Chloride on Alveolar Bone," Calcified Tissue International vol. 35, No. 2 (1983): pp. 258-260.
Grynpas, M.D., et al., "Effects of Low Doses of Strontium on Bone Quality and Quantity In Rats," Bone vol. 11, (1990): pp. 313-319.
International Preliminary Report on Patentability for PCT/US2008/060720 mailed Nov. 5, 2009.
International Search Report and Written Opinion for PCT/US2008/060720 mailed Oct. 22, 2008, 12 pages.
Kendler, D.L., "Strontium Ranelate—Data on Vertebral and Nonvertebral Fracture Efficacy and Safety: Mechanism of Action," Current Osteoporosis Reports vol. 4 (2006): pp. 34-39.
Marie, P.J., et al., "An Uncoupling Agent Containing Strontium Prevents Bone Loss by Depressing Bone Resorption and Maintaining Bone Formation in Estrogen-Deficient Rats", Journal of Bone and Mineral Research vol. 8, No. 5 (1993): pp. 607-615.
Marie, P.J., et al., "Short-term Effects of Fluoride and Strontium on Bone Formation and Resorption in the Mouse," Metabolism vol. 35, No. 6 (1986): pp. 547-551.
Marie, P.J., et al., "Effect of Low Doses of Stable Strontium on Bone Metabolism in Rats," Mineral and Electrolyte Metabolism vol. 11 (1986): pp. 5-13.
Marie, P.J., "Strontium ranelate: A dual mode of action rebalancing bone turnover in favour of bone formation," Current Opinion in Rheumatology vol. 18, Supp. 1 (2006): pp. S11-S15 (2006).
Matsumoto, A., "Effect of strontium chloride on bone resoprtion induced by prostaglandin E2 in cultured bone," Archives of Toxicology vol. 62 (1988): pp. 240-241.
Meunier, P.J., et al., "The Effects of Strontium Ranelate on the Risk of Vertebral Fracture in Women with Postmenopausal Osteoporosis," New England Journal of Medicine vol. 350, No. 5 (2004): pp. 459-468.
Pi, M., et al., "Identification of a Novel Extracellular Cation-sensing G-protein-coupled Receptor," The Journal of Biological Chemistry vol. 280, No. 48 (2005): pp. 40201-40209.
Ratnoff, O.D. et al., "Studies on a Proteolytic Enzyme in Human Plasma: VIII. The Effect of Calcium and Strontium Ions on the Activeation of the Plasma Proteolytic Enzyme," Journal of Experimental Medicine vol. 96 (1952): pp. 319-329. Retrieved from jem.rupress.org on Mar. 3, 2010.
Wu, C., et al., "The effect of strontium incorporation into $CaSiO_3$ ceramics on their physical and biological properties," Biomaterials vol. 28 (2007): pp. 3171-3181.
Zhao, F., et al., "Surface treatment of injectable strontium-containing bioactive bone cement for vertebroplasty," Journal of Biomedical Materials Research Part B: Applied Biomaterials vol. 69, No. 1 (2004): pp. 79-86.
Jones, C. I., et al., 'Differential effects of the iodinated contrast agents Ioxaglate, Iohexol and Iodixanol on thrombus formation and fibrinolysis,' Thrombosis Research, vol. 112, (2003):pp. 65-71.
Menovsky, T., et al., 'Use of Fibrin Glue to Protect Tissue During CO2 Laser Surgery,' The Laryngoscope, vol. 108, (1998):pp. 1390-1393.
Omnipaque 300 Dosing indications. Retrieved on Oct. 8, 2013 from http://reference.medscape.com/drug/omnipaque-iohexol-343760.
Kneser, U., et al., "Fibrin gel-immobilized primary osteoblasts in calcium phosphate bone cement: In vivo evaluation with regard to application as injectable biological bone substitute," 2005, Cells Tissues Organs, vol. 179, pp. 158-169.
Le Guéhennec, L., et al., "A review of bioceramics and fibrin sealant," 2004, European Cells and Materials, vol. 8, pp. 1-11.

(56) References Cited

OTHER PUBLICATIONS

Wittkampf, Albert R.M., "Fibrin glue as cement for HA-granules," 1988, *J. Cranio-Max. Fac. Surg.*, vol. 17, pp. 179-181.

Wittkampf, Albert R.M., "Augmentation of the maxillary alveolar ridge with hydroxylapatite and fibrin glue," 1989, *J. Oral Maxillofac. Surg.*, vol. 46, pp. 1019-1021.

* cited by examiner

INJECTABLE FIBRIN COMPOSITION FOR BONE AUGMENTATION

FIELD OF THE INVENTION

The present invention relates to a biodegradable injectable composition for bone augmentation comprising fibrin, a contrast agent and calcium salt-containing particles, as well as a method for bone augmentation in a patient suffering from a bone disorder comprising injecting said composition into a non-mineralized or hollow portion of said bone.

BACKGROUND OF THE INVENTION

For example, percutaneous bone augmentation includes the techniques of vertebroplasty and kyphoplasty which have been used in the following indications: painful hemangiomas, osteoporotic compression fractures, traumatic compression fractures and painful vertebral metastasis. An example is the percutaneous delivery of polymethylmethacrylate (PMMA) bone cements to repair fractured vertebral bodies. This treatment is effective in relieving pain and restoring height to the vertebrae. The targeted vertebrae are identified using fluoroscopy and a trocar needle is introduced into the vertebral body. The PMMA can be delivered to one (unilateral) or both (bilateral) sides of the vertebral body and the delivery is monitored using fluoroscopy to ensure that the cement remains a bolus, without leakage or migration.

Complications of the technique include leakage of PMMA. This can be paravertebral leakage, venous infiltration, epidural leakage and intradiscal leakage (Truckai C., Shadduck J. H., US 2006089715, 2006). Leakage can result in very serious complications including compression of adjacent structures (requiring further surgery) and/or embolism. Recent research has also demonstrated that a mismatching of forces between the PMMA and natural bone leads to an increase in secondary fractures in the vertebrae adjacent to the PMMA treatment (Trout A. T., Kallmes D. F., Kaufmann T. J., Journal of Neuroradiology, 2006, 27:217-223).

A further complication of the technique is the high exothermicity of PMMA that can potentially cause heat necrosis extending to the dural sac, cord and nerve roots. This exothermicity also limits the ability of PMMA to incorporate any pharmacological or chemotherapeutic agents. PMMA is also a non-resorbable material and is capable of leaching unreacted, unpolymerised and low molecular weight chemicals. For the technique a fluoroscopic contrast agent (usually barium sulphate) is incorporated in the PMMA cements to facilitate the fluoroscopic delivery. The long term effects of barium sulphate on the bone and the cement properties are not fully known.

The viscosity of PMMA is also a critical parameter. It must be low enough to permit injection and high enough to prevent it from being squeezed into the vasculature. The viscosity rises with time providing the clinician with a window of approximately 10 minutes to perform the technique and retrieve the needle.

Thus, a strong need exists for injectable bone augmentation compositions which overcome the above-mentioned disadvantages.

Therefore, it is an object of the present invention to provide new injectable compositions for bone augmentation, such as in vertebroplasty and kyphoplasty.

SUMMARY OF THE INVENTION

The present invention relates to a micro-porous injectable fully resorbable, i.e. biologically degradable, fibrin matrix. The material of the present invention has substantially no exothermicity, exhibits mechanical properties typically seen in elastomers and is mechanically superior to fibrin alone. Adequate radio-opacity is achieved through the incorporation of suitable contrast agents and viscosity is achieved or controlled through the incorporation of a particulate species. Unlike PMMA, in certain embodiments the starting material of the present invention gels rapidly and can be delivered with negligible waiting time. It does not have an upper time limit for completion of the technique allowing more time to deliver the material.

DETAILED DESCRIPTION OF THE INVENTION

One aspect of the present invention relates to a multi-component system for an injectable bone augmentation composition, comprising:
  component (a) comprising fibrinogen;
  component (b) comprising thrombin;
  component (c) comprising at least one contrast agent; and
  component (d) comprising at least one type of calcium salt-containing particles having a diameter of about 200 µm or less.

According to one embodiment of the present invention the components (a) to (d) of the multi-component system as defined above are each present in solution, wherein at least component (a) is spatially separated from component (b).

The multi-component system for an injectable bone augmentation composition as defined above may further include any other component suitable for e.g. augmenting, strengthening, supporting, repairing, rebuilding, healing or filling a bone, such as osteoinductive agents, growth factors, chemotherapeutic or pharmacological agents, biologically active agents, hardening and/or adhesive compounds and mineral additives. These compounds may be contained in any of the components (a) to (d) of the multi-component system according to the present invention or may be comprised as extra components.

According to one example of the present invention, the fibrinogen component (a) of the multi-component system as defined above may further comprise one or more of extracellular matrix proteins, for example fibronectin, cellular associated proteins, other plasma derived proteins, for example blood clotting factor XIII (FXIII) and proteases, and protease inhibitors, and mixtures thereof. The fibrinogen solution according to the present invention may also include any additive which is comprised in the state of the art for scientific and/or commercially available fibrinogen compositions, for example commercially available fibrinogen solutions.

The term "fibrinogen" includes not only fibrinogen per se, but also any clot-forming substance, such as clot-forming derivatives of fibrinogen, for example "fibrin1".

The amount of fibrinogen in said fibrinogen component (a) of the multi-component system ranges for example from about 10 to about 200 mg/ml, such as from about 30 to about 150 mg/ml or from about 75 to about 115 mg/ml.

The thrombin component (b) of the multi-component system according to the present invention, may further comprise additional compounds known in the art as well as one or both of the components (c) and (d), particularly the contrast agent component (c). There is no specific limitation in respect to the used thrombin amount. In one example of the present invention, the amount of thrombin in said thrombin component (b) is such that it is at least about 1 IU/ml in the final clotted composition, such as about 30 IU/ml.

The term "thrombin" includes not only thrombin per se, but also any gelation-inducing or clotting-inducing agent for component (a), for example a physiologically acceptable alkaline buffer system.

The term "contrast agent", as used herein, includes any suitable contrast agent usable according to the present invention in imaging applications known in the art such as fluoroscopy. In one embodiment of the present invention, the suitable contrast agent of the multi-component system as defined above has a low osmolality and allows fibrin assembly to occur at an appropriate extent.

Further, the term "contrast agent" includes all such compounds which can be used according to the present invention and can be distinguished from a surrounding tissue by detecting and/or applying radiation such as X-ray radiation, radioactive radiation, infrared radiation, ultraviolet radiation, electron or neutron radiation, or a magnetic field, or ultrasound, or any combination thereof.

In one example of the present invention, the suitable contrast agent of the multi-component system according to the present invention comprises at least one iodine containing organic compound. In a further example of the present invention, organic compounds containing rare earth elements such as gadolinium can be used.

As used herein, the term "iodine containing organic compound" includes all compounds which contain at least one iodine atom and/or iodine ion, bonded either physically or chemically, for example covalently or coordinatively. The same definition applies mutatis mutandis to the above-mentioned organic compound containing rare earth elements.

Examples of suitable contrast agents of the multi-component system as defined above are selected from the group consisting of diatrizoate (meglumine), iodecol, iodixanol, iofratol, iogulamide, iohexol, iomeprol, iopamidol, iopromide, iotrol, ioversol, ioxaglate and metrizamide.

According to one example of the present invention, the amount of contrast agent such as iodixanol or iohexol in component (c) is such that it ranges from about 100 to about 800 mg/ml, such as from about 150 to about 600 mg/ml or from about 200 to about 400 mg/ml, in the final clotted composition.

The term "particle" includes any type of particle shape or form known in the art, for example spherical, angular or hollow.

In one embodiment of the present invention, the calcium salt-containing particles of the multi-component system according to the present invention are selected from the group consisting of tricalcium phosphate, alpha-tricalcium phosphate, beta-tricalcium phosphate, calcium phosphate, a polymorph of calcium phosphate, hydroxyapatite, calcium carbonate, calcium sulfate and combinations thereof. For example, said calcium salt-containing particles are selected from the group consisting of tricalcium phosphate, alpha-tricalcium phosphate, beta-tricalcium phosphate and calcium phosphate, having a Ca/P ratio in the range from about 1.5 to about 2. The calcium salt-containing particles of the present invention further include all commercially available compounds and/or mixtures known in the art to be used within the meaning of component (d). According to another example, said calcium salt-containing particles of the multi-component system of the present invention have a diameter of less than about 100 µm, for example of less than about 50 µm. In one specific example of the present invention the amount of the particles in component (d) ranges from about 1 to about 50% w/w, such as from about 10 to about 45% w/w or from about 30 to 40% w/w in respect to the final clotted composition.

According to one embodiment of the present invention, the amount of fibrinogen in component (a) of the multi-component system as defined above ranges from about 10 to about 200 mg/ml, the amount of thrombin in component (b) is such that it is at least about 1 IU/ml in the final clotted composition, the amount of contrast agent contained in component (c) is such that it ranges from about 100 to about 800 mg/ml in the final clotted composition, and the amount of the at least one type of calcium salt-containing particles in component (d) ranges from about 1 to about 50% w/w in respect to the final clotted composition.

According to a specific example of the present invention, the amount of fibrinogen in component (a) of the multi-component system as defined above ranges from about 75 to about 115 mg/ml, the amount of thrombin in component (b) is such that it ranges from about 25 IU/ml to about 50 IU/ml in the final clotted composition, the amount of contrast agent contained in component (c) is such that it ranges from about 300 to about 500 mg/ml in the final clotted composition, and the amount of the at least one type of calcium salt containing particles in component (d) ranges from about 30 to about 40% w/w in respect to the final clotted composition.

In another embodiment of the present invention, the multi-component system for an injectable bone augmentation composition, comprises:

component (a) comprising fibrinogen;
component (b) comprising thrombin;
component (c) comprising at least one contrast agent; and
component (d) comprising at least one type of calcium salt-containing particles having a diameter of about 200 µm or less;

wherein one or more or all of the components (a) to (d) are present in a solid form.

The multi-component system according to the present invention may contain the components either in form of a solution or of a dispersion or of a solid, for example as a lyophilisate, or any combination thereof. Further, the components in said multi-component system may be present in containers suitable for storage, transportation or use of said multi-component system. The containers usable in the multi-component system according to the present invention are not limited in any way but include containers of any size, material or shape, for example vials or syringes.

Moreover, the components of said multi-component system may for example be contained in different containers or may be present in the same container in any combination, for example as a combination of components (b) and (c) in one container and of components (a) and (d) each in different containers.

According to the present invention, the containers may for example contain one or more components as a solid, as well as a solvent separated from said components by a separation means in said container, wherein a solution of the respective one or more components can be prepared by breaking or removing said separation means. The components (a) to (d) of the multi-component system of the present invention may be also present as a ready-to-use mixture.

Moreover, said components (a) to (d) present in one or more containers may also be part of a kit, comprising the multi-component system as defined above. The kit may further comprise any additional compound usable in the multi-component system of the present invention, for example auxiliary agents, buffer salts or buffer solutions.

The kit as defined above may also contain means for mixing the components, for example syringes, Luer adapters, tubes, extra containers, etc.

Another aspect of the present invention relates to an injectable bone augmentation composition, comprising:
- component (a) comprising fibrin;
- component (b) comprising thrombin;
- component (c) comprising at least one contrast agent; and
- component (d) comprising at least one type of calcium salt-containing particles having a diameter of about 200 μm or less.

According to one example of the present invention, the injectable bone augmentation composition is prepared from the multi-component system as defined above, for example by mixing the components of said multi-component system together and/or homogenizing said components. The preparation of the injectable bone augmentation composition can be carried out at any suitable temperature, such as in the range from about 18 to about 37° C., for example at 25° C.

Moreover, the injectable bone augmentation composition as defined above may further include any other component suitable for e.g. augmenting, strengthening, supporting, repairing, rebuilding, healing or filling a bone, such as osteoinductive agents, growth factors, chemotherapeutic or pharmacological agents, biologically active agents, hardening and/or adhesive compounds and mineral additives. These compounds and/or agents can be chemically attached to the matrix, adsorbed on the particulate component, for example on the calcium containing particles, trapped in the fibrin matrix or contained as a free molecule/drug particle, for example a powder.

The components (b) to (d) of the injectable bone augmentation composition according to the present invention are the same as defined for the multi-component system characterized above.

The term "fibrin" does not only refer to fully coagulated fibrinogen but further includes any mixture of fibrin and fibrinogen which may occur during formation of fibrin from fibrinogen using thrombin and, thus, includes any ratio of fibrinogen/fibrin and any grade of gelation and/or clotting conceivable as long as it has no negative impact on the final composition injected into the non-mineralized or hollow portion of the bone. The fibrin component (a) of the injectable bone augmentation composition of the present invention further includes fibrin with only a small amount of fibrinogen or without any fibrinogen left in said fibrin. Moreover, the term "fibrin" further includes any partly or fully gelled or clotted form of component (a) as defined above.

According to one example of the present invention, the amount of fibrin in said fibrin component (a) of the injectable bone augmentation composition as defined above ranges from about 5 to about 100 mg/ml, such as from about 15 to 65 mg/ml or from about 30 to 65 mg/ml in the final clotted composition.

According to another example, the amount of fibrin in said fibrin component (a) of the injectable bone augmentation composition of the present invention ranges from about 5 to about 100 mg/ml in the final clotted composition, the amount of thrombin in said thrombin component (b) is at least about 1 IU/ml in the final clotted composition, the amount of contrast agent contained in said contrast agent component (c) ranges from about 100 to about 800 mg/ml in the final clotted composition, and the amount of the at least one calcium salt-containing particles in component (d) ranges from about 1 to about 50% w/w in respect to the final clotted composition.

According to the present invention, the injectable bone augmentation composition as defined above is in a gelled or clotted state and has a viscosity suitable for injecting into a non-mineralized or hollow portion of a bone, and may be applied in a pre-clotted liquid, gelled or clotted state.

As used herein, the term "gelled" means any state of elevated viscosity when compared to the initial state. This can be observed for example in the formation of fibrin from fibrinogen or in a finely dispersed system of at least one solid phase and at least one liquid phase, such as a colloid. Further, the term "gelled" includes all states of gelation known in the art.

The term "clotted" means, for example, a gel comprising fibrin and includes any kind of coagulation state known in the art.

According to the present invention, the viscosity of the injectable composition depends on the application, i.e. the bone disorder to be treated, and is adjusted within the common knowledge of a person skilled in the art. For example, an injectable composition for filling bone cysts contains a lower fibrin amount and/or a lower amount of calcium salt-containing particles. An injectable composition for replacing non-mineralized portions of the bone contains a higher fibrin amount and/or a higher amount of calcium salt-containing particles.

Another aspect of the present invention, relates to a method of augmenting a bone in a patient suffering from a bone disorder, comprising injecting the injectable bone augmentation composition as characterized above, into a non-mineralized or hollow portion of said bone.

As used herein, the term "patient" means a subject suffering from a bone disorder and includes mammals, particularly human beings.

The method of augmenting a bone as defined above is not limited to a certain mode of treatment and includes any kind of injection technique, for example percutaneous injection. According to a specific example of the present invention, the method for augmenting a bone as defined above is percutaneous vertebral augmentation and comprises vertebroplasty and kyphoplasty.

Moreover, the method of augmenting a bone according to the present invention can be used for strengthening, supporting, repairing, rebuilding, healing or filling a bone, for example a bone in a human suffering from a bone disorder.

Examples of such bone disorders are osteoporosis for example in vertebra, hip and fore-arm, or benign and malignant lesions.

The injectable bone augmentation composition according to the present invention is surprisingly advantageous in that it allows injection into a non-mineralized or hollow portion of a bone while the procedure can be monitored by a variety of imaging methods such as fluoroscopy. This fact effectively enables the surgeon/physician to verify the injected composition is in correct place and therefore advantageously avoids severe problems such as leakage of the composition into the blood stream of the patient. Moreover, the addition of calcium salt containing particles to the fibrin based composition surprisingly enhances the contrast given by the contrast agent contained in said composition, thereby advantageously allowing a reduction of the content of said contrast agent. Other beneficial characteristics of the composition comprise the highly advantageous biodegradability of the final clotted composition, the ease of handling and, particularly in form of the multi-component system, long term storage stability and high availability.

The present invention will be further illustrated in the following examples, without any limitation thereto.

EXAMPLES

Example 1

Preparation of Clots Containing Iodinated Contrast Agent and Particles

Materials:

| | |
|---|---|
| Fibrin sealant solution | Freeze dried fibrinogen powder reconstituted with aprotinin solution to a total clottable protein concentration of 91 mg/ml. |
| Iodixanol | 5-[acetyl-[3-[acetyl-[3,5-bis(2,3-dihydroxypropylcarbamoyl)-2,4,6-triiodo-phenyl]-amino]-2-hydroxy-propyl]-amino]-N,N'-bis(2,3-dihydroxypropyl)-2,4,6-triiodo-benzene-1,3-dicarboxamide |
| Iohexol | 5-(acetyl-(2,3-dihydroxypropyl)amino)-N,N'-bis(2,3-dihydroxypropyl)-2,4,6-triiodo-benzene-1,3-dicarboxamide |
| Particles | Tricalcium phosphate particles (TCP), 35 μm, spherical (Plasma Biotal, Derby UK) |
| Thrombin 500 IU/ml | Freeze dried thrombin powder reconstituted with 5 ml of thrombin buffer, to a concentration of 500 IU/ml. |
| Thrombin Buffer | 40 mM $CaCl_2$ in $H_2O$ |

Either an 80% or a 60% contrast agent (iodixanol or iohexol) and a 75 IU/ml thrombin solution is prepared in a thrombin dilution buffer (40 mM $CaCl_2$ in double distilled water). The solution is then homogenised. The solution is centrifuged to remove bubbles and sterilised by filtering through a 0.22 μm filter. The fibrinogen is mixed with thrombin/contrast agent (CA) in a 1:1 ratio (therefore the CA concentration in the gelled clot is halved to either 40 or 30%). For this 2 ml of the thrombin/contrast agent solution is transferred to a 5 ml syringe. 2 ml of fibrinogen (91 mg/ml) is transferred to a separate 5 ml syringe. The particles (ca. 2 μm) are incorporated as percentage weight of the final clot volume (w/v). These are weighed and placed into another 5 ml syringe.

The syringes containing the particles and the thrombin are connected via a Luer adapter and the thrombin/CA and particles homogenised by transferring the contents from syringe to syringe thoroughly.

The syringes containing the thrombin/CA/particles and the fibrinogen are connected via a Luer adapter and the contents homogenised.

The material remains liquid for approximately 1 minute during this time it can be injected into the defect or alternatively after a few minutes it can be delivered as a pre-formed gel.

Figure 1:
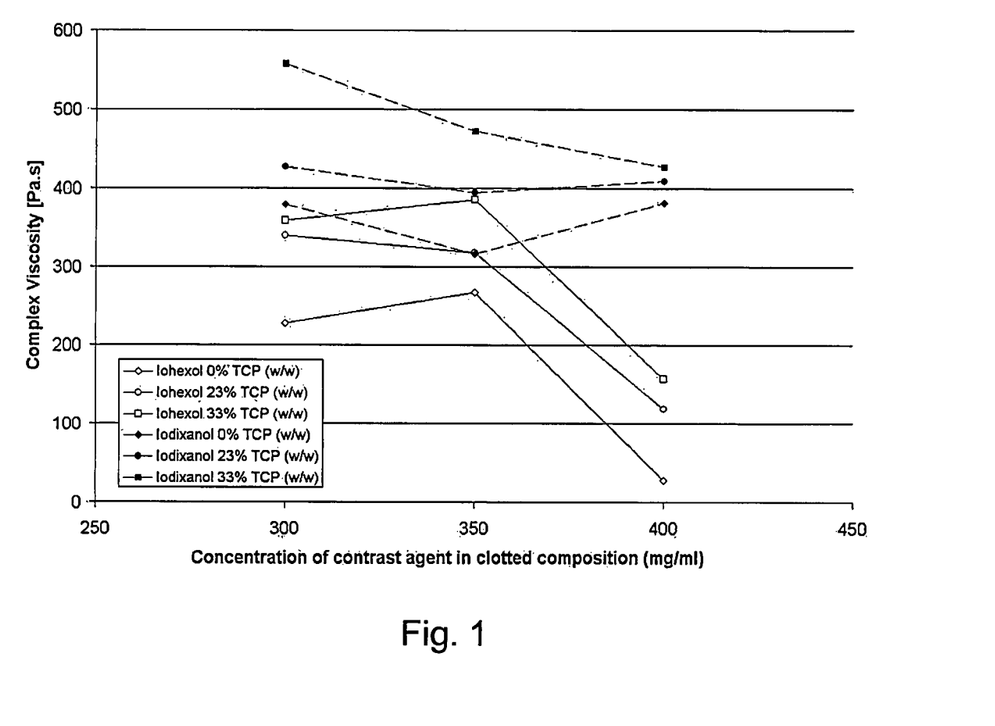
FIG. 1: Differences in complex viscosities as a result of increasing concentration of contrast agent and/or the particulate content.

The viscosities of respective clots with different concentrations of contrast agents and of TCP can be taken from FIG. 1.

Example 2

Mechanical Behaviour of Fibrin Clots in the Presence or Absence of a Contrast Agent Clots containing iodinated contrast agent and particles are prepared as described in Example 1. These clots are cast in wells of a multiwell-plate where they are then allowed to gel. These clots are removed from the wells, and their mechanical properties are then tested in compression using a universal mechanical testing system.

On visual inspection, there is a big difference between normal fibrin clots and CA clots prepared according to Example 1. The contrast agent containing clots are clear and transparent while the normal fibrin clots are white and opaque. Like the normal fibrin clots the CA clots can be injected into a mould following a brief mixing and allowed to gel. Differences between normal clots and CA clots can be observed during this process. The normal clots are easily damaged, collapse and leak buffer while being retrieved from the mold. The CA clots remain intact and can be handled more forcefully. These materials also exhibit elasticity and this is demonstrated using non-confined uni-axial compressive testing. In this test the normal clots reach ca. 80% strain before stress begins to increase. At the point at which the stress rises the clot is near to being completely squashed and the buffer forced out. Conversely CA clots are much stiffer and after 20% strain begin to show an increase in stress i.e. a greater force is needed to compress them and this continues to rise until the clot breaks. If the stress is removed at any point prior to the break the clot returns to its original shape, unlike the normal clots which are permanently damaged. It is also observed that with longer "gelling" times the clots have fewer tendencies to break as they become even more elastic. This often results in experiments having to be stopped as the clots are expelled from the Instron (mechanical testing machine) due to the build up of stored energy.

Example 3

Application of the Injectable Bone Augmentation Composition

Osteoporosis and age related loss in bone mineral density often leads to fractures in vertebra and femoral head. Injection of the injectable bone augmentation composition according to the present invention at these sites helps in the treatment of such injuries. The formulations of the injectable bone augmentation compositions are prepared as outlined in Example 1.

Under fluoroscopy (C-arm) a vertebroplasty trocar (diameter: 3.2 mm (10 G) or 1.8 mm (15 G), length 100 or 150 mm) is placed in a vertebra and a femoral head, respectively, of a human cadaver using the transpedicular approach.

TCP is added to the contrast agent containing thrombin solution by swooshing the two components back and forth until homogenization (about 20 times).

The TCP and contrast agent containing thrombin solution is mixed with the fibrinogen solution by swooshing the solutions back and forth approx. 6 times in two connected syringes. After gelation the material (approx. 9 ml) is loaded into the barrel of a vertebroplasty gun (Optimed Cemento RE).

Figure 2:
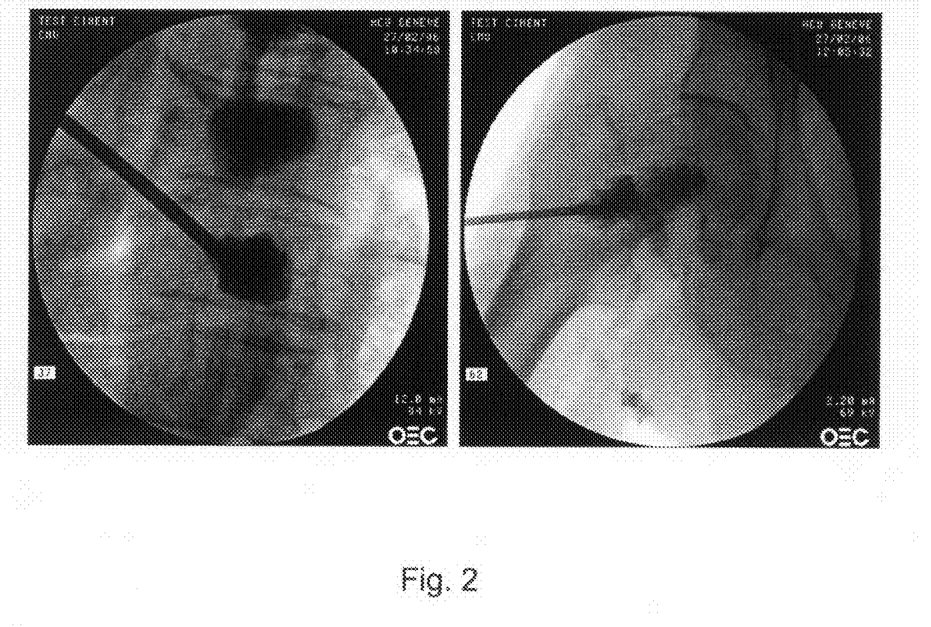
FIG. 2: Injection of the injectable bone augmentation composition into osteoporotic bones to increase local bone production in vertebra (left) and femoral head (right).

The gun is directly connected to the trocar (without a tube in between) and the material is applied to the vertebra and to the femoral head, respectively, by screwing it out of the gun. During the procedures pictures were taken (cf. FIG. 2).

Example 4

In Vivo Studies of the Injectable Bone Augmentation Composition in Sheep

The medial fascia of the tibia shaft is excised and the tibia is exposed. A plate is contoured to the shaft and fixed to the bone using screws. The plate is removed again and a standardized 1 cm full thickness defect is created. The segment is removed, the plate is repositioned and the screws are reinserted. Thereafter, the injectable bone augmentation composition is filled into the defect and the wound is closed by suture.

The animals are followed up for 4, 8 and 12 weeks (X-ray evaluation). At the 12 weeks timepoint the animals are sacrificed and the tibia is extracted for final analysis (μCT and histology).

The contrast agent had no negative impact on the medical effect of the clot inside the bone.

We claim:

1. A multi-component system for preparing an injectable bone treatment composition, comprising:
    component (a) comprising fibrinogen;
    component (b) comprising thrombin; and
    component (c) comprising at least one contrast agent selected from the group consisting of iodixanol and iohexol;
    wherein one or more or all of the components (a) to (c) are present in a solid form, and
    wherein the amount of contrast agent is from 300 to 400 mg/ml in the composition.

2. An injectable bone treatment composition, comprising:
    component (a) comprising fibrin;
    component (b) comprising thrombin;
    component (c) comprising at least one contrast agent selected from the group consisting of iodixanol and iohexol; and
    wherein the amount of contrast agent is from 300 to 400 mg/ml in the composition.

3. The injectable bone treatment composition according to claim 2, further comprising at least one type of calcium salt-containing particles, wherein the calcium salt-containing particles are selected from the group consisting of tricalcium phosphate, alpha-tricalcium phosphate, beta-tricalcium phosphate, calcium phosphate, a polymorph of calcium phosphate, hydroxyapatite, calcium carbonate, calcium sulfate and any combinations thereof.

4. The injectable bone treatment composition according to claim 3, wherein the calcium salt-containing particles are selected from the group consisting of tricalcium phosphate, alpha-tricalcium phosphate, beta-tricalcium phosphate and calcium phosphate, and mixtures thereof, and/or wherein said calcium salt containing particles have a Ca/P ratio in the range of about 1.5 to about 2.

5. The injectable bone treatment composition according to claim 2, wherein the amount of fibrin in component (a) ranges from about 5 to about 100 mg/ml in the composition.

6. The injectable bone treatment composition according to claim 2, wherein the amount of thrombin in component (b) is at least 1 IU/ml in the composition.

7. The injectable bone treatment composition according to claim 2, wherein the amount of fibrin in component (a) ranges from about 5 to about 100 mg/ml in the composition, and the amount of thrombin in component (b) is at least about 1 IU/ml in the composition.

8. The injected bone treatment composition according to claim 2, wherein said composition is in a gelled or clotted state and has a viscosity suitable for injecting into a non-mineralized or hollow portion of a bone.

9. The multi-component system according to claim 1, wherein the amount of fibrinogen in said fibrinogen component (a) ranges from about 10 to about 200 mg/ml.

10. The multi-component system according to claim 1, wherein the amount of thrombin in said thrombin component (b) is such that it is at least about 1 IU/ml in the composition.

11. The multi-component system according to claim 1, wherein the amount of fibrinogen in component (a) ranges from about 10 to about 200 mg/ml, and the amount of thrombin in component (b) is such that it is at least about 1 IU/ml in the composition.

12. The system according to claim 1, further comprising:
    component (d) comprising at least one type of calcium salt-containing particle having a diameter of about 200 μm or less, wherein the amount of the at least one type of calcium salt-containing particle ranges from about 1 to about 50% w/w in respect to the composition.

13. The multi-component system according to claim 1, further comprising a calcium salt containing particle, wherein the calcium salt is selected from the group consisting of tricalcium phosphate, alpha-tricalcium phosphate, beta-tricalcium phosphate, calcium phosphate, a polymorph of calcium phosphate, hydroxyapatite, calcium carbonate, calcium sulfate and any combinations thereof.

14. The multi-component system according to claim 13, wherein the calcium salt containing particle has a Ca/P ratio in the range from about 1.5 to about 2.

15. The multi-component system according to claim 13, wherein the calcium salt-containing particle has a diameter of less than about 100 μm.

16. The multi-component system according to claim 13, wherein the calcium salt-containing particle has a diameter of less than about 50 μm.

17. The injectable bone treatment composition according to claim 2, further comprising at least one type of calcium salt-containing particle having a diameter of about 200 μm or less, wherein the amount of the at least one type of calcium salt-containing particle ranges from about 1 to about 50% w/w in respect to the composition.

18. The injectable bone treatment composition according to claim 2, further comprising at least one type of calcium salt-containing particle present within a range from about 10 to about 45% w/w in respect to the composition.

19. The injectable bone treatment composition according to claim 2, further comprising at least one type of calcium salt-containing particle present within a range from about 30 to about 40% w/w in respect to the composition.

20. The injectable bone treatment composition according to claim 2, further comprising at least one type of calcium salt-containing particle having a diameter of less than 100 μm.

21. The injectable bone treatment composition according to claim 2, further comprising at least one type of calcium salt-containing particle having a diameter of less than 50 μm.

22. The multi-component system according to claim 1, wherein component (a) comprises the fibrinogen at a concentration of 91 mg/ml, and component (b) comprises thrombin at a concentration of 75 IU/ml.

23. The multi-component system according to claim 1, wherein the components (a) to (c) are present in solution and at least component (a) is spatially separated from component (b).

24. The multi-component system according to claim 1, further comprising an amount of tricalcium phosphate particles having a diameter of about 35 μm, wherein the amount of the tricalcium phosphate particles ranges from about 1 to about 50% w/w in respect to the composition.

25. The multi-component system according to claim 1, further comprising at least one type of calcium salt-containing particle present within a range from about 10 to about 45% w/w in respect to the composition.

26. The multi-component system according to claim 1, further comprising at least one type of calcium salt-containing particle present within a range from about 30 to about 40% w/w in respect to the composition.

* * * * *